(12) United States Patent
Liu

(10) Patent No.: US 7,273,521 B1
(45) Date of Patent: Sep. 25, 2007

(54) METHOD OF PRODUCING GRANULATED CALCIUM CARBONATE/CALCIUM PHOSPHATE COMPOSITE MATERIALS WITH VERY HIGH CALCIUM TO PHOSPHATE MOLE RATIOS

(75) Inventor: Sung-Tsuen Liu, Aberdeen, MD (US)

(73) Assignee: J.M. Huber Corporation, Edison, NJ (US)

(*) Notice: Subject to any disclaimer, the term of this patent is extended or adjusted under 35 U.S.C. 154(b) by 0 days.

(21) Appl. No.: 11/414,028

(22) Filed: Apr. 28, 2006

(51) Int. Cl.
| | |
|---|---|
| C09C 1/02 | (2006.01) |
| C01B 25/32 | (2006.01) |
| C01B 31/24 | (2006.01) |
| A61K 9/16 | (2006.01) |
| A61K 9/20 | (2006.01) |
| A61K 9/48 | (2006.01) |

(52) U.S. Cl. ............ 106/462; 106/464; 423/305; 423/306; 423/430; 424/451; 424/464; 424/489

(58) Field of Classification Search ............ 106/462, 106/464; 423/305, 306, 430; 424/451, 464, 424/489
See application file for complete search history.

(56) References Cited

U.S. PATENT DOCUMENTS

| | | | |
|---|---|---|---|
| 2,882,127 A | | 4/1959 | Baron et al. |
| 3,068,067 A | | 12/1962 | Aia |
| 3,095,269 A | | 6/1963 | Chiola et al. |
| 3,294,486 A | | 12/1966 | Cremer et al. |
| 3,409,394 A | | 11/1968 | Sprigg et al. |
| 3,538,230 A | | 11/1970 | Pader et al. |
| 4,483,837 A | * | 11/1984 | Cremer et al. ............ 423/309 |
| 4,707,361 A | | 11/1987 | Gustafson et al. |
| 4,755,367 A | | 7/1988 | Brachtel et al. |
| 5,024,825 A | * | 6/1991 | Buhl et al. ............ 423/309 |
| 5,108,728 A | | 4/1992 | Rau et al. |
| 5,348,745 A | | 9/1994 | Daher et al. |
| 5,427,755 A | * | 6/1995 | Dany et al. ............ 423/309 |
| 5,427,756 A | * | 6/1995 | Dany et al. ............ 423/309 |
| 5,759,575 A | | 6/1998 | Gergely et al. |

FOREIGN PATENT DOCUMENTS

FR   2529187 A   *  12/1983

OTHER PUBLICATIONS

Derwent Acc No. 1978-46676A, abstract of Japanese Patent Specification No. 53-056174A (May 22, 1978).*
English Language Translation of JP 53-056174 (May 22, 1978).*

* cited by examiner

Primary Examiner—Anthony J. Green
(74) Attorney, Agent, or Firm—Carlos Nieves; William Parks

(57) ABSTRACT

A new and useful method of simultaneously producing and granulating composite materials for simultaneous internal delivery of high amounts of calcium and phosphate to a subject (person or animal) is provided. Such a method entails the dropwise addition of concentrated phosphoric acid within a specified amount of water into a vessel containing a powdered material of lime and/or calcium carbonate, with the lime and/or calcium carbonate present in an excessive amount of the phosphoric acid, with subsequent, mixing, drying, milling, and sieving to provide the correct target particle size range for the resultant granulated materials. Such specifically produced granulated calcium carbonate/dicalcium phosphate materials exhibit very high available calcium levels, very high available phosphate levels, excellent flow characteristics, and very high capability for compression into tablets. Products including such particularly produced composite materials are also encompassed within this invention.

11 Claims, No Drawings

METHOD OF PRODUCING GRANULATED CALCIUM CARBONATE/CALCIUM PHOSPHATE COMPOSITE MATERIALS WITH VERY HIGH CALCIUM TO PHOSPHATE MOLE RATIOS

The present invention relates generally to a new and useful method of simultaneously producing and granulating composite materials for simultaneous internal delivery of high amounts of calcium and phosphate to a subject (person or animal). Such a method entails the dropwise addition of concentrated phosphoric acid within a specified amount of water into a vessel containing a powdered material of lime and/or calcium carbonate, with the lime and/or calcium carbonate present in an excessive amount of the phosphoric acid, with subsequent, mixing, drying, milling, and sieving to provide the correct target particle size range for the resultant granulated materials. Such specifically produced granulated calcium carbonate/dicalcium phosphate materials exhibit very high available calcium levels, very high available phosphate levels, excellent flow characteristics, and very high capability for compression into tablets. Products including such particularly produced composite materials are also encompassed within this invention.

BACKGROUND OF THE INVENTION

Calcium phosphate is the base structure of bones within vertebrates. Hydroxyapatite, also known as $Ca_5(PO_4)_3OH$, constitutes a very large percentage of calcium phosphate in this manner, and has been utilized as a nutritional supplement for people in jeopardy of suffering osteoporosis. Such a supplement has proven effective by simultaneously permitting sufficient absorption and use of both the calcium and phosphate components thereof by the subject user. Calcium absorption alone has proven, in some studies, to be lacking in terms of combating bone depletion and/or thinning. The ability to delivery and permit absorption of relatively large amounts of phosphate at the same time has proven to function properly as a manner of protecting a user from osteoporosis and other bone maladies. It has also been observed that the lack of phosphate absorption during possible calcium absorption may actually impact the effectiveness of the calcium supplement by itself. Since hydroxyapatite is the main structural component of bone, and thus includes both calcium and phosphate therein, such a result is not surprising.

Another potential supplement to aid with osteoporosis issues is $Ca_4P_2O_9$. Such a compound exhibits a mole ratio of calcium to phosphate (Ca/P) of about 2.0. Hydroxyapatite exhibits such a Ca/P mole ratio of about 1.67. Other compounds, such as dicalcium phosphate alone, exhibit mole ratios well below 1.0. It is believed that this high mole ratio of Ca to P is necessary to generate sufficient bone protection and treatment through nutritional supplement use. Unfortunately, both hydroxyapatite and $Ca_4P_2O_9$ are rather complicated to manufacture and thus relatively expensive for utilization within the nutritional supplement industry. A manner of supplying the industry with a high Ca/P mole ratio (i.e., between 1 and 10) supplement source with low complexity of production and thus lower cost than these standard supplement products is thus highly desirable. Furthermore, a simple method of permitting production of any desired Ca/P mole ratio product would be highly desirable as well. To date, however, no such method and/or product has been accorded the nutritional supplement industry.

BRIEF DESCRIPTION OF THE INVENTION

It has now been determined that the highly desired, but previously unavailable, improvements in granulated calcium carbonate/dicalcium phosphate composite materials as noted above may be obtained through a method of reacting concentrated phosphoric acid mixed with specified amounts of water with an amount of powdered material of lime and/or calcium carbonate in excess of that by weight of the phosphoric acid, allowing the reaction thereof to form composite material calcium carbonate/dicalcium phosphate granulates, and collecting, drying, and sieving the granulates. Such a method, described in greater detail below, actually provides the advantage of producing composite materials exhibiting very high Ca/P mole ratios (excess of 1.0, for instance), and, depending upon the selected amount of calcium carbonate starting materials as compared with the amount of phosphoric acid reactant, such Ca/P mole ratios may be adjusted as desired, all within a single reaction step (but with subsequent drying, milling, and sieving procedures to collect the granulates made therefrom). Such a method thus accords the producer a time-, cost-, and resource-efficient manner of making the desired granulated calcium carbonate/dicalcium phosphate end-product composites without having to first provide a powder and thus avoiding the any subsequent granulation steps thereafter. As a result, as well, no binders are needed to provide such granulated materials and relatively low amounts of introduced water (for example, from 30 mL to 80 mL of water per 350 g of calcium carbonate used) are required to effectuate the target production method. Although such binders may not be required, they can optionally be added to provide greater reliability of dimensional stability of the formed tablets, if desired. Such binders include polymeric species, such as carboxymethyl cellulose, and the like, as one possible, non-limiting example. The overall finished product then not only exists in granulated form, but such materials exhibit excellent flow properties and high amounts of available calcium therein. Such free flow properties also result in the ability to easily dispense the granulates uniformly into capsules with little to no dusting and/or lack of control (and thus possible waste of material) during filling of individual capsules and uniformly feed into an automatic tablet press. Furthermore, another advantage of this method, and thus the resultant dicalcium phosphate granulates made therefrom, is the compressibility of the granulates into tablets for ingestion by a patient/user as well, particularly due to such materials exhibiting brittle fraction during compaction. Additionally, the granulated materials may be milled upon production and collection into powders.

Accordingly, this inventive granulation method entails the steps of a) providing a preselected weight of a solid material selected from the group consisting of lime and calcium carbonate and any mixtures thereof; b) introducing a preselected weight of concentrated phosphoric acid to the solid material of step "a", wherein said concentrated phosphoric acid is first diluted with an amount of water of from 30 mL to 80 mL per 350 g of the calcium carbonate of step "a"; c) mixing the resultant solution of step "b"; d) collecting the resultant particles from mixing step "c", and e) drying said resultant particles of step "d". Also encompassed within this invention is a calcium carbonate/dicalcium phosphate granulate exhibiting a Ca/P mole ratio of from 1 to 10; preferably from 1 to 5; more preferably from 1 to 3.5.

DETAILED DESCRIPTION OF THE INVENTION

For the purposes of this description, the term "calcium carbonate powder" and any variations thereof, is intended to encompass any powdered material of calcium carbonate, including ground calcium carbonate and precipitated calcium carbonate. The term "concentrated phosphoric acid" is intended to encompass a solution of phosphoric acid in liquid form with at most 15% by weight of water present. Thus, such a concentrated acid will exhibit a very high molarity and/or concentration (at least 85% concentration). Such an acid should be introduced slowly (i.e., dropwise) within the solid (i.e., powdered) lime or calcium carbonate sample. The amount of calcium carbonate or lime should exceed, in terms of a stoichiometric 1:1 ratio, that of the concentrated phosphoric acid prior to introduction of water to the acid. The calcium carbonate is present in any amount, dependent upon the size of the reaction vessel employed, as long as sufficient volume is permitted for addition of sufficient amounts of acid and water for the desired invention method reaction to occur. The amount of acid used will ultimately determine the Ca/P mole ratio of the final granulated composite materials made therefrom. The lower the acid amount, the greater the Ca/P mole ratio. Thus, for example, and without any intention of limiting the breadth of the invention, if 350 g of calcium carbonate is utilized, then 290 g of concentrated phosphoric acid (with about 50 mL of water added to the acid prior to the reaction) added dropwise will generate a calcium carbonate/dicalcium phosphate composite granulate exhibiting a Ca/P of about 1.39. If an amount as low as 20.6 g of the acid is used (with about 40 mL of water), then the Ca/P mole ratio will be approximately 20.

The inventive method is relatively simple to follow, which is yet another advantage. Basically, a starting calcium carbonate powder or lime powder is obtained initially. To this powder is added the concentrated phosphoric acid in the amount noted above. Such introduction of phosphoric acid may be performed through any means, including, without limitation, drop-wise addition while stirring, if in smaller batch sizes, or in repetitive streams of the liquid solution at set intervals and in set volumes for each repeated introduction. The rate of addition should be performed in a range of anywhere between 0.1 to 100 ml/min per 350 g of lime or calcium carbonate (or, between 0.000285 to 0.285 ml/min per gram of calcium carbonate), preferably slower, of from 1 to 25 ml/min per 350 g of lime or calcium carbonate. This repetitive introduction step is potentially preferred as it permits reaction of the concentrated phosphoric acid in discrete areas within the provided lime or calcium carbonate powder to best ensure, while stirring, that substantially uniform reaction and resultant granulation occurs. Spraying of the phosphoric acid solution on the powder while or with subsequent stirring is also possible. The granulation may be performed in any apparatus known in the industry such as mixers having low shear or high shear, fluid bed technology, and the like.

The amount of concentrated phosphoric acid to be added to the provided lime or calcium carbonate powder must conform to the stoichiometric ranges as noted previously. Specific volumes to be added are not critical as the important feature is to properly introduce the phosphoric acid at intervals or through a steady, slow stream while the powder is properly stirred, and in a stoichiometric amount.

Subsequent to reaction of the two components, the wet mixture is then collected and dried. This drying step may be performed within any well known apparatus, including, without limitation, a rotary dryer, an oven, a fluid bed drier, and the like. The purpose for drying is to remove the excess water through evaporation to leave a granulated solid dehydrated dicalcium phosphate in particulate form. Such a dried particulate may then be milled, again with any standard well known apparatus, including, without limitation, a hammer mill, a ball mill, an air mill, a bead mill and the like. The milled particulate can then either be separated through a sieve to provide narrow ranges of particle size materials, or coupled with any fines separated through sieving. Such sieving thus may be utilized as either a particle size sequestration means, or to ensure the granulates are reduced to their smallest particle sizes, or even to permit generation of dicalcium phosphate powders for use as potentially desired.

The flow properties of the granulates have proven excellent and exceed a FLODEX measurement of 14, at the most, preferably at most 10. Such flow properties indicate the facility of transporting such granulates without appreciable cohesion or other packing characteristics occurring during manufacture, after storage, and the like.

In the past, the typical manner of producing anhydrous dicalcium phosphate involved the initial precipitation of either anhydrous (dehydrated) or dihydrated dicalcium phosphate by introducing lime or calcium carbonate into a vessel of diluted phosphoric acid, followed by the separation via filtration of the resultant precipitated solid from the mixture, drying the resultant particles, and then subsequent granulation of the collected fine particles. Subsequently, if the dihydrate was formed, thorough drying was necessary to drive of the water to provide the ultimate dehydrated form. Such an involved method was not only cumbersome to perform, but required multiple steps that resulted in increased manufacturing costs, and involved large amounts of potential dangerous phosphoric acid. The inventive method thus is a significant improvement not only in terms of manufacturing of calcium phosphate materials, but also in terms of providing the aforementioned high Ca/P mole ratio composite materials.

The traditional processing methods, and thus the closest prior art to such a novel method, are taught within U.S. Pat. No. 3,095,269 (preparation by precipitating the product from a slurry of lime and dilute phosphoric acid which has been heated above 80° C.), U.S. Pat. No. 3,068,067 (preparation by precipitation from a mother liquor containing a combination of monoammonium phosphate with ammonium and calcium chloride), and U.S. Pat. No. 3,353,908 (preparation from a monoalkali metal phosphate solution in combination with gypsum in a mill). Such specific dehydrated dicalcium phosphate materials are, however, unsuitable in dry direct compression as the particles are too fine and will not flow properly into the compression dies. Furthermore, such compounds cannot meet U.S. Pharmacopeia (U.S.P.) standards without further treatment as they contain ammonium, chloride or sulfate ions, nor may these anhydrous compositions be dry granulated to make a dry direct compression tableting composition. The inventive one-step method and dehydrated dicalcium phosphate products made therefrom are thus significant improvements over these typical procedures and materials.

Once produced, the desired inventive high Ca/P mole ratio calcium carbonate/dicalcium phosphate composite granulated materials can then be introduced into desired end use formulations and/or forms. For instance, the resultant granulated composite materials may be used as produced and introduced into gelatin capsules to provide a calcium supplement for a patient/user. Such a supplement may be utilized as a delivery system for calcium (for various reasons and/or purposes, such as a manner of treating osteoporosis, as one non-limiting example), among other various uses, both as a direct supply of calcium, phosphate, or both, or as a carrier for other materials. Tablets or lozenges may also be produced from such materials through compression techniques as well. Such tablets may utilize solely the inventive granulated dicalcium phosphate materials, or may include certain binders or other additives that act as compression aids to improve the friability of such a tablet formulation. Such binders or compression aids may include, without limitation, gum acacia, maltodextrin, alginic acid, gelatin, guar gum, povidone, pregelatinized starch, glucose, ethylcellulose, carboxymethyl cellulose, microcrystalline cellulose, and hydroxypropyl methylcellulose.

Other additives may be present within either a tablet or capsule form including the inventive dicalcium phosphate materials depending on the nature of the end use selected. Thus, pharmaceutical actives may be present, including any number of analgesics, acid scavengers, cold remedies and the like. Additional dietary supplement ingredients may be present such as essential minerals (potassium, magnesium, selenium, iron, and the like), vitamins, folic acid, niacin and the like. Excipients may be added to tablets to aid in quick tablet disintegration when placed in the buccal cavity as well. Such excipients include, without limitation, crospovidone, MCC, sodium starch glycolate and calcium silicate, such as RXCIPIENT® FM1000 from J.M. Huber Corporation. Other additives possible within such formulations include coatings (such as cellulose ethers, gums, and the like) over the tablet or lozenge surface, sweeteners, diluents, flavoring agents, colorants, preservatives, other antacid compounds (such as aluminum hydroxide, magnesium hydroxide, magnesium carbonate, and the like), and other typical additives for such orally administered dicalcium phosphate tablet compositions.

PREFERRED EMBODIMENTS OF THE INVENTION

The following non-limiting examples are provided as guidelines to follow in the manufacture of the inventive high Ca/P mole ratio composite materials.

Granulate Formation

Granules of a calcium phosphate having different mole ratios of Ca:P were formed by introducing 350 g ground calcium carbonate, HUBERCAL® 250 available from J.M. Huber Corporation, Quincy, Ill., into Hobart mixing tank and thereafter adding phosphoric acid solution dropwise with mixing on medium speed during a period of about 20 minutes. The phosphoric acid solution was prepared by mixing a specified quantity of 85% phosphoric acid with a specified quantity of water. Quantities of ingredients are specified in Table 1 below. The formed wet granules were then oven dried at 100° C. overnight. The dried granules were passed through a 20 mesh (850 µm) sieve. The granules which did not pass through the 20 mesh sieve were gently milled with a mortar and pestle, sieved through the 20 mesh sieve and combined with the granules which previously passed through the sieve.

The granules prepared in the examples above were tested for flowability, particle size distribution and X-ray diffraction (XRD) for composition according to the methods described below. The evaluation results are summarized in Table 1.

The intrinsic flowability, which is the property of a powder to flow evenly under the action of gravity and other forces, was determined using a FLODEX tester available from Hanson Research, Chatsworth, Calif. The FLODEX tester is comprised of a funnel with stopper to hold the test powder, under which is a straight-walled open cylinder and finally one of a series of plates with increasing orifice sizes. The FLODEX tester was assembled with the plate having the smallest orifice size and 50 g of the sample was placed in the stoppered funnel. After 30 seconds the stopper was removed and if the sample flowed through the orifice, the size of the orifice diameter, in mm, was recorded as the FLODEX index. If the sample did not flow through the orifice, the sample was placed back in the funnel and the experiment was repeated with plates of increasing orifice size until the sample flowed through an orifice. The diameter of the smallest orifice needed for flow was recorded as the FLODEX index. This test simulates how materials will flow, i.e. to feed a tableting machine. Generally, products with FLOWDEX numbers of less than about 20 have good flow properties.

The particle size distribution was evaluated by placing the 100 g of granules on a stack of U.S. sieves selected from 20 mesh (850 µm), 50 mesh (180 µm), 100 mesh (150 µm), 120 mesh (125 µm), 140 mesh (105 µm), and 200 mesh (75 µm) with the sieves having the largest openings at the top, i.e. in the order listed with the 20 mesh sieve on top and 200 mesh sieve at the bottom. The sieves were placed on a Boerner Portable Sieve Shaker, Model RX-24, available from W.S. Tyler, Inc., Mentor, Ohio, and shaken for 5 minutes after which the screens were separated and the granules on each utilized sieve were weighed.

Composition crystalline phase was determined by powder X-Ray Diffraction (XRD) by comparing diffractograms of the example materials to known diffractograms for calcium carbonate/dicalcium phosphate materials denoted in the table as "CC/DCP".

TABLE 1

Reaction Conditions and Characteristics of Composite Materials

| Example | 1 | 2 | 3 | 4 | 5 | 6 |
|---|---|---|---|---|---|---|
| $CaCO_3$, g | 350 | 350 | 350 | 350 | 350 | 350 |
| 85% $H_3PO_4$, g | 290 | 290 | 202 | 133.7 | 133.7 | 106.7 |
| $H_2O$, ml | 50 | 50 | 60 | 60 | 80 | 80 |
| Ca/P mole ratio | 1.39 | 1.39 | 1.73 | 3.01 | 3.01 | 3.8 |
| % Particles >850 µm | 0.1 | 0.1 | 0.2 | 0.5 | 0.6 | 0.5 |
| % Particles 850-180 µm | 22.2 | 22.2 | 25.6 | 34.1 | 52.8 | 52.2 |
| % Particles 180-150 µm | 32.6 | 31.3 | 27 | 23 | 26.3 | 26.8 |
| % Particles 150-105 µm | 16.9 | 16.1 | 14.4 | 12.3 | 7.5 | 7.2 |
| % Particles 105-75 µm | 13.8 | 13.4 | 12.5 | 16 | 5.3 | 6 |
| % Particles <75 µm | 14.1 | 16.9 | 20.3 | 19.5 | 7.4 | 7.2 |
| Flodex Index, mm | 4 | 5 | 5 | 10 | 6 | 14 |
| XRD Identification | CC/DCP | CC/DCP | CC/DCP | CC/DCP | CC/DCP | CC/DCP |

Examples 1 and 2 were duplicates having a mole ratio of 1.39 mole calcium to moles of Phosphorus and very similar granule size distributions. Examples 3 to 6 had increasing mole ratio of Ca to Phosphorus of from about 1.7 to about 3.8. All of these example granules had acceptable flow properties.

Tablet Production and Testing

Directly compressible excipient granules made in Examples 1, 4, and 6 were compressed into tablets and several properties of the formed tablets were evaluated. Tablets were prepared by weighing all formulation ingredients (97.5% DCP and 2.0% croscarmellose sodium) together, except the lubricant magnesium stearate, on a weighing pan. The combined ingredients were passed through a 20 mesh (850 µm) sieve to remove any lumps and then the resulting mixture was transferred to a PK-V blender (twin shell dry blender model 014-215-0053, available from Patterson Kelly, East Stroudsburg, Pa.) and mixed for 5 minutes. The magnesium stearate lubricant (0.5%) was then geometrically diluted with the mixture and then added back to the PK blender and all ingredients mixed together for an additional 2 minutes.

Tablets were produced from the resulting formulation on an 8-station Piccola rotary tablet press available from Riva S.A., Argentina, fitted with 10 mm standard concave die punches compacting at 10 kN, 20 kN and 30 kN compression forces. Tablet weight was maintained at about 800 mg by adjusting the tablet press. Tablet ejection force was measured by the tablet press instrumentation software. Tablet properties were measured according to the method described below and the results are summarized in Table 4.

All tablets were prepared 24 hours before testing weight, hardness, thickness, disintegration time and friability.

Tablet hardness, expressed in kP, was measured on 5 tablets utilizing an Erweka TBH30 instrument (Milford, Conn.) and the result reported was an average of 5 measurements.

Tablet disintegration time (DT) was determined according to the USP test for uncoated tablets by placing 3 tablets (each tablet in a separate tube) in an Erweka ZT72 disintegrator (Milford, Conn.). The tablets were repeatedly immersed in 37° C. deionized water at a rate of 30 strokes per minute until the tablets disintegrated, as detected and recorded by the instrument. The reported result was an average of the measurements.

Tablet friability was determined by placing 10 tablets in a Distek, Inc. Friabilator DF-3 (North Brunswick, N.J.) set for 100 revolutions. The % friability is calculated from the amount of tablet weight lost (friable) by weighing the tablets before and after rotation.

TABLEs 2 and 3, below present these tablet properties. Tablets 1 and 1A were made from the same batch of Example 1, above, with different compression forces used to produce the target tablets. Tablets 4 and 4A, and 6 and 6A were analogously produced.

TABLE 2

Tablet Properties

| Tab. # | Target Comp. Force (kN) | Actual Comp. Force (kN) | Aver. Tab. Weight (mg) | Aver. Tab. Hardness (kp) | Hardness % CV |
|---|---|---|---|---|---|
| 1 | 15 | 15.7 | 821 | 11.21 | 15.58 |
| 1A | 30 | 29.7 | 802 | 29.33 | 11.03 |
| 4 | 15 | 15.6 | 828 | 12.41 | 16.59 |
| 4A | 30 | 29.7 | 815 | 27.51 | 5.72 |
| 6 | 15 | 14.5 | 815 | 14.67 | 11.95 |
| 6A | 30 | 30.2 | 818 | 32.80 | 9.89 |

TABLE 3

Tablet Properties (Continued)

| Tablet # | Average Disintegration Time (seconds) | Disintegration Time % CV | % Friability |
|---|---|---|---|
| 1 | 10 | 11.0 | 0.524 |
| 1A | 10 | 11.0 | 0.150 |
| 4 | 9 | 9.4 | 0.495 |
| 4A | 14 | 7.8 | 0.147 |
| 6 | 9 | 0.0 | 0.319 |
| 6A | 13 | 6.1 | 0.171 |

When this granulation was compressed at 20-30 kN compaction pressure, the tablets demonstrated acceptable physical characteristics performance, such as high tablet hardness and low tablet friability. Tablet hardness, friability and ejection forces were acceptable for tablets compressed on 10 mm tooling. The fast disintegration test results seen in the test formulation indicates that this excipient does not negatively impact this important tableting criterion. It is demonstrated by the very reproducible tablet weights that the excellent flow properties of this inventive product provides uniform die fill during tableting and is suitable for use as a directly compressible excipient.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of producing a calcium carbonate/dicalcium phosphate composite material exhibiting a Ca/P mole ratio of greater than 1.0 comprising the steps of
   a) providing a solid material selected from the group consisting of lime and calcium carbonate and any mixtures thereof;
   b) introducing an amount of concentrated phosphoric acid to the solid material of step a) to form a resultant solution of said solid materials and said concentrated phosphoric acid, wherein said concentrated phosphoric acid is first diluted with an amount of water of from 30 mL to 80 mL per 350 g of the solid material of step a), and wherein said concentrated phosphoric acid is added in an amount in which the stoichiometric ratio of said solid material of step a) to said concentrated phosphoric acid is greater than 1;
   c) mixing the resultant solution of step b) to form resultant particles of said calcium carbonate/dicalcium phosphate composite materials;
   d) collecting said resultant particles from mixing step c), and
   e) drying said resultant particles of step d).

2. The method of claim 1 wherein the introduction of the concentrated phosphoric acid in step b) is accomplished through dropwise addition at a rate of from 0.1 to 100 ml/min per 350 grams of lime and/or calcium carbonate powder material.

3. A calcium carbonate/dicalcium phosphate granulate exhibiting a Ca/P mole ratio of from 1 to 20.

4. The granulate of claim 3 exhibiting a Ca/P mole ratio of from 1 to 5.

5. The granulate of claim 4 exhibiting a Ca/P mole ratio of from 1 to 3.5.

6. A tablet or capsule comprising the granulate of claim 3.

7. A tablet or capsule comprising the granulate of claim 4.

8. A tablet or capsule comprising the granulate of claim 5.

9. The tablet or capsule of claim 6 further comprising at least one fatty acid salt and optionally comprising at least one binder.

10. The tablet or capsule of claim 7 further comprising at least one fatty acid salt and optionally comprising at least one binder.

11. The tablet or capsule of claim 8 further comprising at least one fatty acid salt and optionally comprising at least one binder.

* * * * *